US010881365B2

(12) United States Patent
Vogtmeier et al.

(10) Patent No.: US 10,881,365 B2
(45) Date of Patent: Jan. 5, 2021

(54) SYSTEM AND METHOD FOR MULTI-BEAM X-RAY EXPOSURE FOR 4D IMAGING

(71) Applicant: KONINKLIJKE PHILIPS N.V., Eindhoven (NL)

(72) Inventors: Gereon Vogtmeier, Aachen (DE); Klaus Juergen Engel, Veldhoven (NL); Michael Grass, Buchholz in der Nordheide (DE); Bernd Menser, Hauset (BE); Heidrun Steinhauser, Eindhoven (NL); Alberto Fazzi, Eindhoven (NL); Herman Stegehuis, Best (NL); Dirk Schaefer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/099,285

(22) PCT Filed: May 12, 2017

(86) PCT No.: PCT/EP2017/061421
§ 371 (c)(1),
(2) Date: Nov. 6, 2018

(87) PCT Pub. No.: WO2017/194727
PCT Pub. Date: Nov. 16, 2017

(65) Prior Publication Data
US 2019/0209107 A1 Jul. 11, 2019

(30) Foreign Application Priority Data
May 13, 2016 (EP) ...................... 16169586

(51) Int. Cl.
*A61B 6/00* (2006.01)

(52) U.S. Cl.
CPC .............. *A61B 6/4007* (2013.01); *A61B 6/54* (2013.01); *A61B 6/4291* (2013.01); *A61B 6/482* (2013.01); *A61B 6/503* (2013.01); *A61B 6/5241* (2013.01)

(58) Field of Classification Search
CPC ...... A61B 6/482; A61B 6/4007; A61B 6/4291; A61B 6/503; A61B 6/5241; A61B 6/54;
(Continued)

(56) References Cited

U.S. PATENT DOCUMENTS 4,566,112 A   1/1986 Linde
5,305,363 A * 4/1994 Burke ................... A61B 6/032
                                                              378/10
(Continued)

FOREIGN PATENT DOCUMENTS

DE   102010040308 A1 *  3/2012  .......... A61B 6/4458
DE   102010040308 A1     3/2012
(Continued)

*Primary Examiner* — Chih-Cheng Kao

(57) ABSTRACT

An interventional X-ray system is proposed, the system including a multi X-ray source unit positioned below a patient table. This 'multiblock' may comprise several x-ray sources with focal spot positions distributed along the x-y (table) plane. The x-ray sources are operable in a switching scheme in which certain x-ray sources may be activated in parallel and also sequential switching between such groups is intended. The switching may be carried out so that several images with different projection angles can be acquired in parallel. In other words, an optimal multi-beam X-ray exposure is suggested, wherein fast switching in one dimension and simultaneous exposure in the 2nd dimension is applied.

20 Claims, 4 Drawing Sheets

(58) Field of Classification Search
CPC ............... G06T 11/008; G06T 2200/04; G06T 2207/10116
See application file for complete search history.

(56) References Cited

U.S. PATENT DOCUMENTS

| | | | |
|---|---|---|---|
| 2006/0039532 A1* | 2/2006 | Wu | G01N 23/04 378/62 |
| 2006/0285633 A1 | 12/2006 | Sukovic | |
| 2010/0002829 A1* | 1/2010 | Dafni | A61B 6/032 378/9 |
| 2010/0034450 A1 | 2/2010 | Mertelmeier | |
| 2010/0080342 A1* | 4/2010 | Takahashi | G01N 23/046 378/22 |
| 2010/0329416 A1 | 12/2010 | Tsujii | |
| 2012/0330134 A1* | 12/2012 | Helm | A61B 6/032 600/424 |
| 2013/0308746 A1 | 11/2013 | Ueki | |
| 2014/0023178 A1 | 1/2014 | Kim | |
| 2016/0345919 A1* | 12/2016 | Kim | A61B 6/4007 |

FOREIGN PATENT DOCUMENTS

| | | |
|---|---|---|
| KR | 1020140013403 A | 2/2014 |
| WO | 2015119466 A1 | 8/2015 |

\* cited by examiner

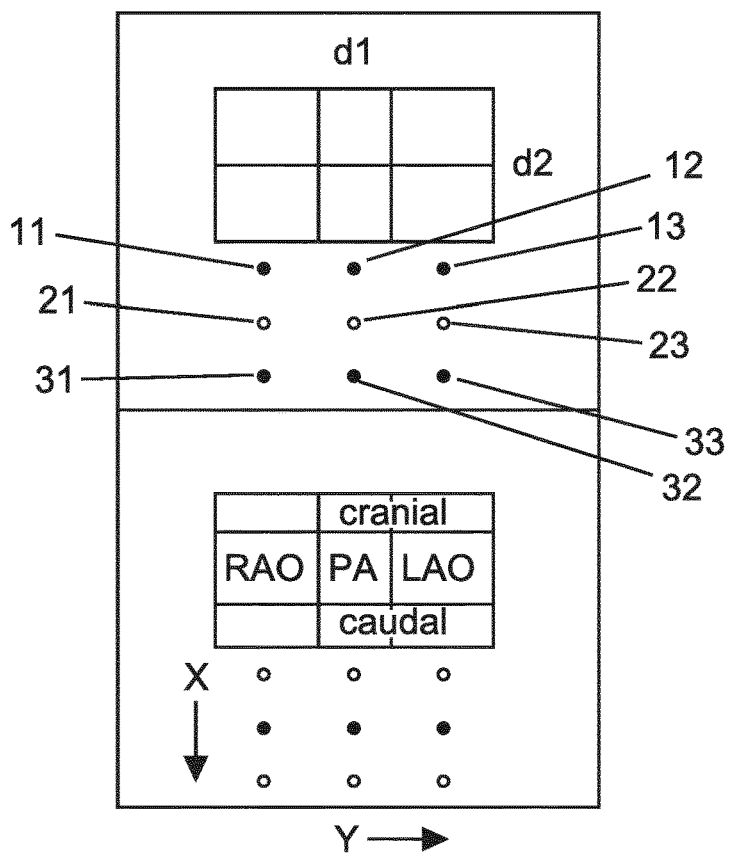
Fig. 3a
Fig. 3b
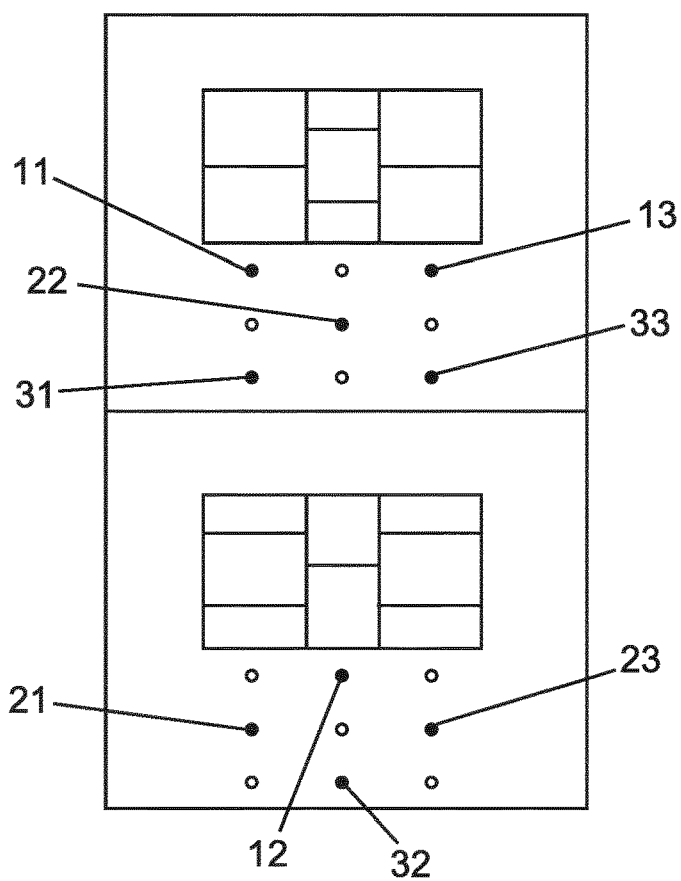
Fig. 4a
Fig. 4b

SYSTEM AND METHOD FOR MULTI-BEAM X-RAY EXPOSURE FOR 4D IMAGING

CROSS-REFERENCE TO PRIOR APPLICATIONS

This application is the U.S. National Phase application under 35 U.S.C. § 371 of International Application No. PCT/EP2017/061421, filed on May 12, 2017, which claims the benefit of European Patent Application No. 16169586.1, filed on May 13, 2016. These applications are hereby incorporated by reference herein.

FIELD OF THE INVENTION

The invention generally relates to a system and a method for a multi-beam X-ray exposure for 4D imaging. Particularly, the invention relates to a system and a method for a multi-beam X-ray exposure for 4D imaging in cardiology by applying fast switching in a first dimension and simultaneous exposure in a second dimension.

BACKGROUND OF THE INVENTION

For interventional procedures, an X-ray imaging configuration may be provided in which a 2-dimensional array of sources simultaneously irradiates a large detector. In such a configuration, the required size of the detector may be problematic, further this approach suffers from cross-scatter. Otherwise, conventionally C-arm X-ray systems have been used for interventional procedures. But the C-arm is a bulky device that requires quite some space next to the patient and table. In particular, when performing a 3D scan, access to the patient is not possible and equipment has to be positioned outside the C-arm movement range.

SUMMARY OF THE INVENTION

In view of the above mentioned problems, it can be seen as an object of the invention to solve the above problems or at least to mitigate these problems.

These and further objects are solved by the subject-matter of the respective independent claims. Further embodiments are described in the dependent claims.

In general, a simplified interventional X-ray system is proposed, in particular for percutaneous coronary interventions (PCI) and other minimally invasive cardiac procedures. The system may include a multi X-ray source unit positioned below the patient table. This 'multiblock' may comprise several x-ray sources with focal spot positions distributed along the x-y (table) plane. The x-ray sources are operable in a 'hybrid' switching scheme, wherein certain x-ray sources defining groups may be activated simultaneously and also sequential switching between such groups may be carried. In other words, sources belonging to a single group are activated simultaneously, whereas sources belonging to different groups are activated in an alternating manner.

The switching may be carried out so that several images with different projection angles can be acquired simultaneously. In other words, an optimal multi-beam X-ray exposure is suggested, wherein fast switching in one dimension and simultaneous exposure in the 2nd dimension is applied. This way, the number of angular views may be enlarged in the switching dimension and cross-scatter and detector size may be limited while the advantages of simultaneous exposure are mostly kept.

In accordance with an embodiment, a system comprises a plurality of radiation sources, and a radiation detector, wherein each of the radiation sources is arranged so as to emit radiation onto a sub-area of the detector. A first group of radiation sources out of the plurality of radiation sources is configured to simultaneously emit radiation onto a first pattern of sub-areas of the detector and a second group of radiation sources out of the plurality of radiation sources is configured to simultaneously emit radiation onto a second pattern of sub-areas of the detector. The sub-areas of the first pattern overlap the sub-areas of the second pattern. On the other hand, the sub-areas in one pattern do not overlap each other.

The radiation detector may be a single detector defining a plurality of sub-areas, but may also be a combination of more than one detector, i.e. may consist of multiple parts. Further, the sub-areas may or may not be defined by respective parts of the detector.

According to an embodiment, the radiation sources of the system may be arranged in a matrix extending in a first direction and in a second direction. The first and second directions may in particular be seen when viewed from the detector onto the matrix of the radiation sources. In such a view, the radiation sources of a first group of radiation sources may be arranged substantially along the first direction of the matrix. The first direction may be oriented perpendicular to the second direction, but the first and second directions may also have an angle other than 90° relative to each other.

According to an embodiment, the radiation sources of a second group of radiation sources may be arranged substantially along the first direction of the matrix, like a first group of radiation sources. However, the radiation sources of the second group of radiation sources may also be arranged with a distance in the second direction from the radiation sources of the first group of radiation sources.

According to another embodiment, the plurality of radiation sources includes a plurality of groups of radiation sources. Beside so-called first and second groups, at least one further group of radiation sources may emit radiation onto a further pattern of sub-areas of the detector, wherein the sub-areas of the further pattern may overlap the sub-areas of at least one of the other patterns of sub-areas. Consequently, in an embodiment with four or five groups of radiation sources, the sub-areas of each of the respective pattern of sub-areas will not overlap each other, whereas the sub-areas of different groups may overlap. A repeated utilization of areas of the detector in a sequence of radiation pattern allows for a relatively small detector.

According to an embodiment, the plurality of radiation sources defines a main radiation direction and at least one radiation source of the plurality of radiation sources is arranged so that the radiation direction of that radiation source is inclined relative to the main radiation direction. The radiation direction of a radiation source may be inclined relative to the main radiation direction with an angle of up to 50°. Having inclined radiation sources allows generating projection images through a region of interest in a body from different angles without moving the multiblock with the array of radiation sources. For example, a first radiation direction may be inclined by 45° from a right side and a second radiation direction may be inclined by 45° from a left side, so that two images can be provided having radiation directions being perpendicular to each other. Images with radiation directions being inclined with respect to each other may be utilized to generated 3D images of a region of interest.

According to a further embodiment, the system comprises a plurality of high voltage generator units which are configures to provide different voltages for different radiation sources. The high voltage provided by the generator units may be controllable so that images may be generated which provide additional image information, for example for spectral decomposition. Also means for fast kV switching may be included.

Furthermore, the system may comprise an anti-scattering grid at the radiation detector. Depending on the intended distribution of the sub-areas, the anti-scattering grid may be arranged to provide a better separation of the sub-areas from each other, for example to ensure that the sub-areas of one pattern do not overlap.

According to a further embodiment, the detector may be configured to process up to 120 fps (frames per second). A detector which is configured to process a high number of frames per second allows a fast switching between different radiation pattern of sub-areas. As a consequence, when considering for example an imaging of a beating heart, it is possible to provide images generated from different directions during virtually a single phase of the heartbeat.

The system may further comprise a control unit configured to control a switching sequence of radiation emission from the groups of radiation sources. A sequence of radiation emission may be an iterative sequence like $1^{st}$ group, $2^{nd}$ group, and optionally $3^{rd}$ group to $n^{th}$ group. A sequence of radiation emission may otherwise be an arbitrary sequence of the groups, like $1^{st}$ group, $3^{rd}$ group, $4^{th}$ group, $2^{nd}$ group, $2^{nd}$ group, $5^{th}$ group in an example with five groups of X-ray sources, and so on. Keeping in mind that detector sub-areas of a radiation pattern of radiation originating from sources within one group shall not overlap each other, the actual sequence may be defined on the basis of the location and orientation of each of the radiation sources forming one group of radiation sources. The detector may be divided into a plurality of sections in one direction, and within each section a plurality of sub-areas may be defined in another direction, which sub-areas overlap each other and onto which radiation is emitted from radiation sources of different groups of radiation sources.

According to another aspect, a method of using a system as described above may comprise the steps of emitting simultaneously radiation from a first group of radiation sources, detecting the emitted radiation on a first pattern of sub-areas of the detector, emitting simultaneously radiation from a second group of radiation sources, and detecting the emitted radiation on a second pattern of sub-areas of the detector, wherein the sub-areas of the first pattern overlap the sub-areas of the second pattern.

According to an embodiment, the method may further comprise the step of reconstructing a first image based on the radiation detected in at least one of the sub-areas of the first pattern and the step of reconstructing a second image based on the radiation detected in at least one of the sub-areas of the second pattern.

According to another embodiment, the method may further comprise the step of providing different high voltages to different radiation sources. This may allow for spectral decomposition. Depending on the voltage, a radiation source will emit more or less radiation, and depending on the amount of radiation, specific structures of a body of interest can be visualized. Thus, images may be generated which allow a visualization of different structures almost at the same time, i.e. by a fast switching between different radiation sources operated with different voltages.

According to an embodiment, a switching between the step of emitting radiation from a first group and the step of emitting radiation from a second group may be performed within 30 ms, preferably within 16 ms or even faster.

Based on images generated from directions being inclined relative to each other, a 3D image may be generated.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited. It is in particular noted that the above described embodiment are described based on specific and differing features and that a combination of those features, i.e. of these embodiments may also be of advantage.

BRIEF DESCRIPTION OF THE DRAWINGS

FIGS. 3a and 3b illustrate a first example of a sequence of two radiation pattern, based on nine radiation sources forming two groups of radiation sources.

FIGS. 4a and 4b illustrate a second example of a sequence of two radiation pattern, based on nine radiation sources forming two groups of radiation sources.

The illustrations in the drawings are schematically only and not to scale. It is noted that similar elements are provided with the same reference signs in different figures, if appropriate.

DETAILED DESCRIPTION OF EMBODIMENTS

Figure 1:
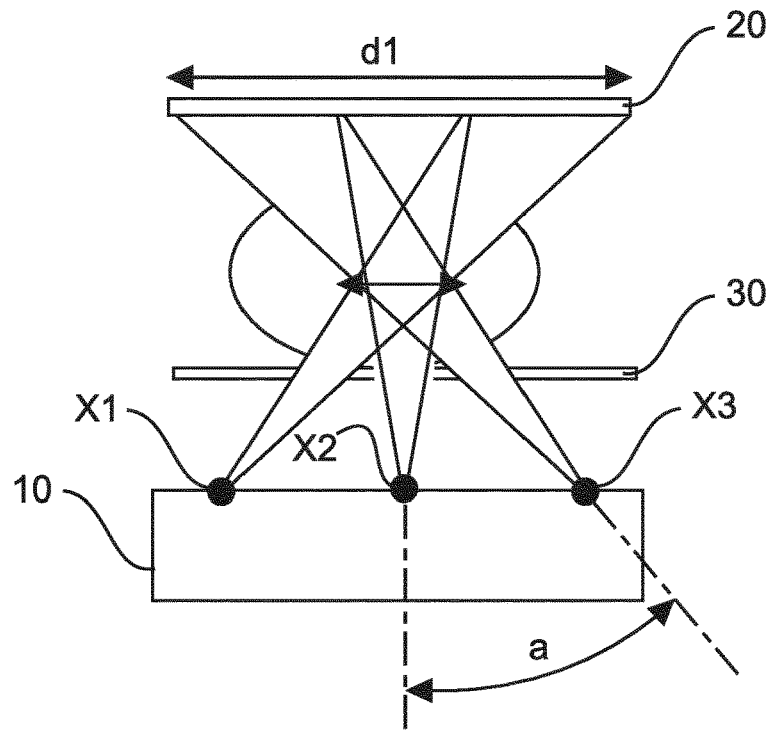
FIG. 1 illustrates aspects of a first embodiment of a system from a first viewing direction.
Figure 2:
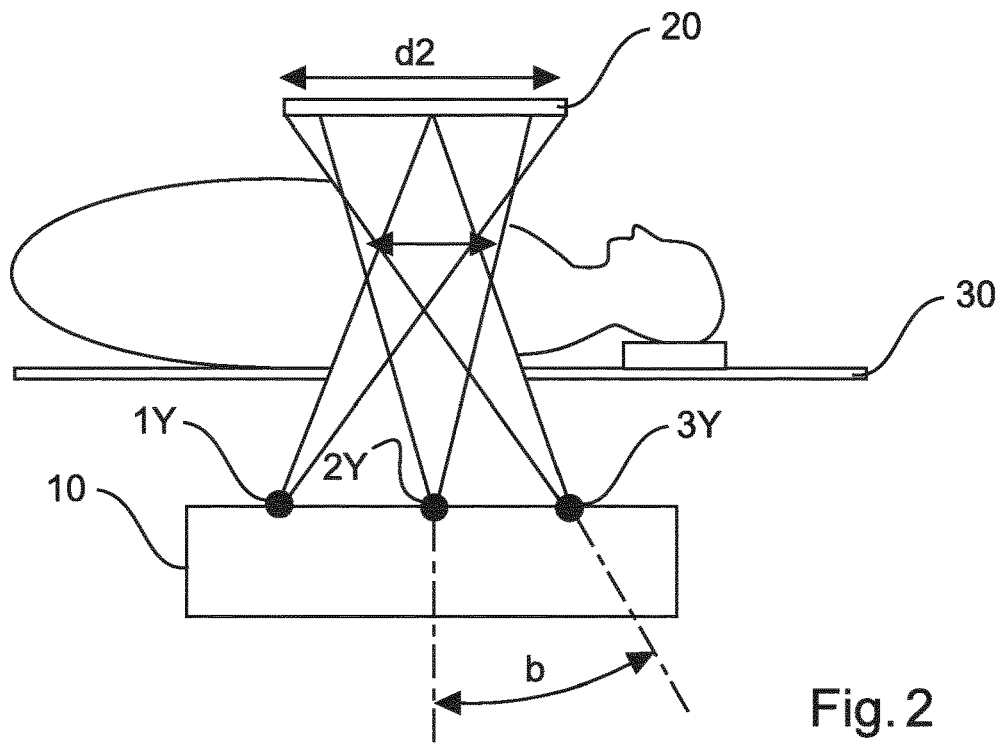
FIG. 2 illustrates aspects of the first embodiment from a second viewing direction.

FIGS. 1 and 2 illustrate aspects of a system in accordance with a first embodiment. The system comprises a multiblock 10 with radiation sources X1, X2 and X3 shown in FIG. 1 and radiation sources 1Y, 2Y and 3Y shown in FIG. 2, and a detector 20. The array of radiation sources is flat, i.e. is in one plane.

FIG. 1 illustrates a slice in a plane transverse to a longitudinal direction of a patients table 30. In this slice, three radiation sources X1, X2 and X3 are present side by side. The radiation source X1 is inclined so as to emit radiation from the left side under the patient table 30 through a patient and to the right side of the surface of the detector 20. The radiation direction of the radiation source X1 may also be indicated as left anterior oblique (LAO). The radiation source X3 is also inclined, but to the opposite of the radiation source X1, and emits radiation from the right side under the patient table 30 through the patient and to the left side of the surface of the detector 20. The radiation direction of radiation source X3 may be indicated as right anterior oblique (RAO). The radiation source X2 is located in the middle under the patient table 30 and emits radiation with a radiation direction perpendicular to the detector surface.

In the context of the embodiments, a main radiation direction can be defined based on the radiation directions of the plurality of radiation sources, as an average of all radiation directions. For example, in FIG. 1 the radiation direction of the radiation source X2 is vertical, whereas the radiation direction of the radiation source X3 is inclined with an angle "a" relative to the radiation direction of the radiation source X2. On the other hand, the radiation direction of the radiation source X1 is inclined opposite to the radiation direction of radiation source X3 when considered relative to the radiation direction of the radiation source X2. An average or mean value of the radiation directions can be seen in this example as a main direction which is parallel to the radiation direction of the radiation source X2. Alternatively, one might consider the radiation directions as vectors, wherein a vector forming the main direction would be calculated as a sum of all vectors of all radiation sources.

As can be seen in FIG. 1, the detector 20 extends in a direction transverse to the longitudinal direction of the patient table 30 with the length d1. As can be seen in FIG. 2, the detector 20 extends in a longitudinal direction of the patient table 30 with a length d2 which length differs from the length d1. In the example of FIGS. 1 and 2, the length d2 is smaller than the length d1.

FIG. 2 illustrates a side view onto the system according to the first embodiment and onto the side of the patient table 30. An orientation of the multiblock 10 with the radiation sources 1Y, 2Y, 3Y, and of the detector 20 is indicated by the terms "cranial" and "caudal" which indicate directions to the head and to the feet of the patient, respectively. The radiation source 2Y is arranged in the middle of the multiblock 10 and a radiation direction of this radiation source is perpendicular to the patient table 30 as well as to a surface of the detector 20. The radiation source 1Y is arranged with an offset to the radiation source 2Y and a radiation direction of this radiation source is inclined relative to the radiation direction of the radiation source 2Y. On the other side, a radiation source 3Y is arranged, also with an inclined radiation direction, wherein the radiation direction of the radiation source 3Y is indicated as being inclined by the angle "b" relative to the radiation direction of the radiation source 2Y.

Each of the radiation sources in FIGS. 1 and 2 emit the respective radiation with a cone angle, i.e. the radiation is emitted not as parallel beams but opens to a certain extent so that the sub-area on the detector surface which is exposed to the radiation is greater than the actual opening at the radiation source. Shutter elements may be provided at a radiation source defining a specific size and shape of the radiation fan. The radiation sources are configured to emit radiation with fan angles so that some sub areas not overlap whereas others overlap each other. In the example of FIGS. 1 and 2, the sub-areas of the radiation sources X1 and X3 do not overlap, also the sub-areas of the radiation sources 1Y and 3Y do not overlap. Otherwise, the sub-areas of the radiation sources X2 and 2Y overlap the respective sub-areas of the other radiation sources.

FIGS. 3a and 3b show schematically an arrangement of the radiation sources of the multiblock 10 as well as a partitioning of the detector surface into sub-areas. In FIG. 3a, the length D1 of the detector surface (as shown in FIG. 1) and the length D2 (as shown in FIG. 2) indicate the dimensions of the detector surface with six sub-areas on it. Furthermore, corresponding radiation sources 11, 12 and 13 (first row), 21, 22 and 23 (second row), and 31, 32 and 33 (third row) are shown. The six sub-areas on the detector surface may for example detect radiation emitted by the radiation sources of the first and third rows. In FIG. 3b, the directions relative to a patient are indicated on the detector surface, i.e. cranial, RAO, PA, LAO and caudal. Here, the general numbering of the radiation sources is indicated by arrows X and Y. Each radiation sources has a two-digit reference sign, with the first digit indicating the position in X direction and the second digit indicating the position in Y direction. Consequently, the radiation sources X1, X2, X3 in FIG. 1 are three radiation sources in one line extending in the Y direction, and the radiation sources 1Y, 2Y, 3Y in FIG. 2 of three radiation sources in one column extending in the X direction.

In the example of FIGS. 3a and 3b, an approach is illustrated in which a 2D array is divided into sub-arrays, wherein 2 or more exposures may be carried out, with one sub-array of sources is active in each exposure. For example, in the 3×3 source array, in a first exposure the six sources in the outer rows, i.e. the first and third row of the array may be used, followed by a second exposure in which the three sources in the center or second row may be used. Effectively, this approach uses simultaneous exposure in one direction (the row direction) and fast switching in the other direction (the column direction).

Another exposure scheme which may be realized based on a 3×3 array of radiation sources is illustrated in FIGS. 4a and 4b. In a first exposure, the radiation sources at the corners of the array, radiation sources 11, 13, 31, 33, as well as the radiation source in the middle, radiation source 22, may be used, followed by a second exposure based on the remainder of sources, radiation sources 12, 21, 23 and 32. On the respective detectors surfaces in FIGS. 4a and 4b, a distribution of sub-areas is shown, which corresponds to the pattern of the emitting radiation sources in the first and second exposure, respectively.

Figure 5:
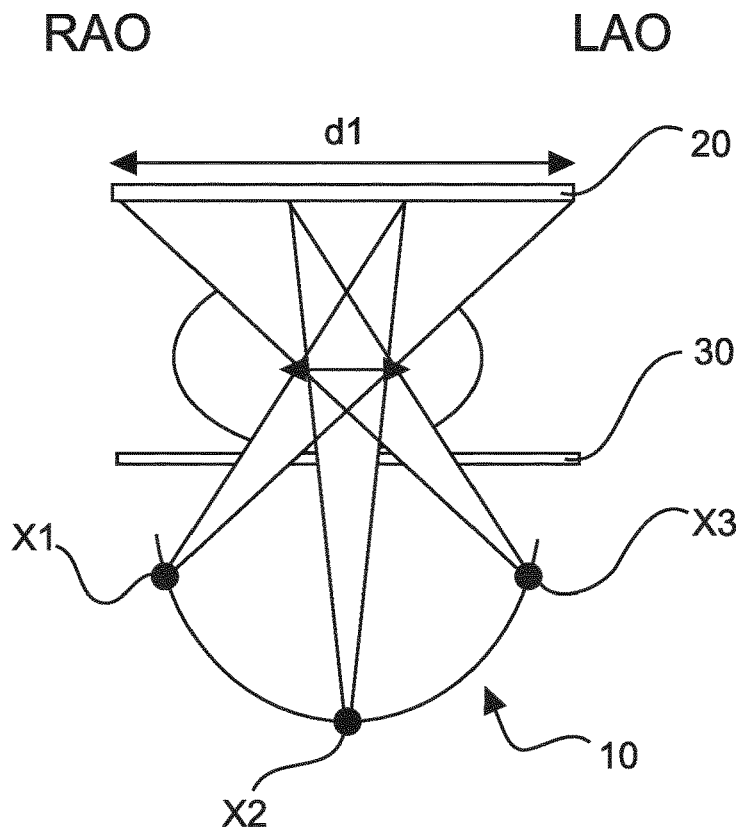
FIG. 5 illustrates aspects of a second embodiment of a system from a first viewing direction.
Figure 6:
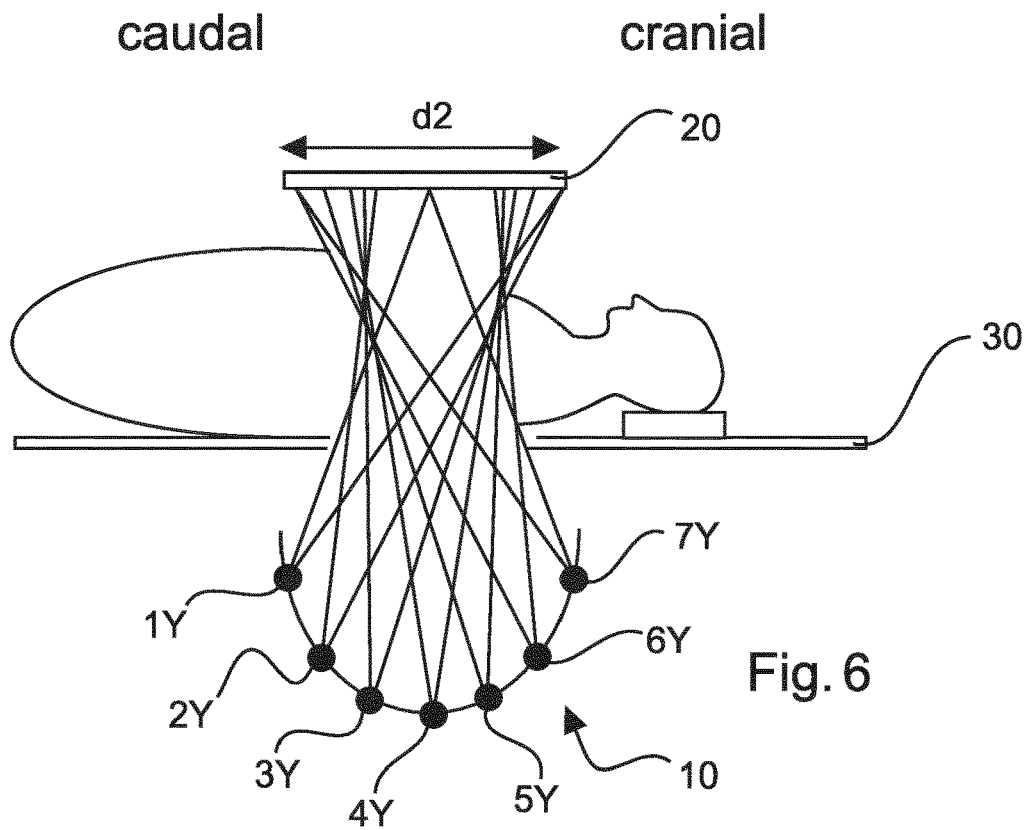
FIG. 6 illustrates aspects of the second embodiment from a second viewing direction.

FIGS. 5 and 6 show a second embodiment of a system. Here, the system comprises an array of radiation sources with seven lines (X) and three columns (Y). Like the first embodiment, the system according to the second embodiment comprises a flat detector 20 extending with a length d1 transverse to the longitudinal direction of the patient table and with a length d2 in the longitudinal direction of the patient table.

In contrast to the first embodiment, the radiation sources in accordance with the second embodiment are arranged along curved lines. At least the lines of radiation sources shown in FIGS. 5 and 6, respectively, are curved. It will be understood that the radius of curvature may vary, not only in different embodiments but also from one line to another line of a single embodiment. Furthermore, the radiation sources may be arranged along straight lines in the X direction and along curved lines in the Y direction, or vice versa. For example, an embodiment may be formed based on a combination of FIGS. 2 and 5.

The arrangement of radiation sources along curved lines provides the possibility to arrange the radiation sources in a body of a multiblock 10 with an orientation of the radiation direction being perpendicular to the outer surface of the multiblock body surrounding the opening of the respective radiation source, with the advantage that smooth surfaces may be easier cleaned for a use of the device in a medical environment.

Figure 7:
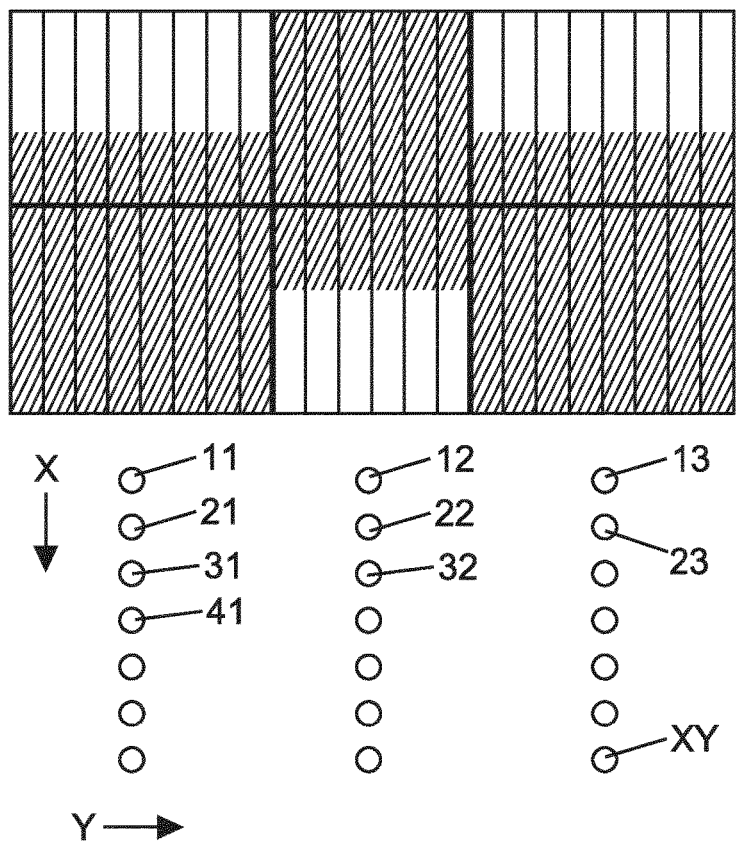
FIG. 7 illustrates general aspects of examples of sequences of radiation patterns.

FIG. 7 shows an exemplary distribution of seven radiation sources in an x direction and three radiation sources in a y direction. It is indicated in that figure how the numbering of the radiation sources is made in the context of this disclosure, from 11 to XY. Consequently, it is intended to encompass all possible numbers of radiation sources in an array of x times y radiation sources. For example, the concept can be realized based on a scheme with 4 exposures for an array of 15 source (5×3), or generally n exposures for a 3×(n+1) array of sources. A trade-off between number of exposures (a higher number having the drawbacks of the fast switching approach) and cross-scatter (which is a problem for simultaneous switching) can be decided per specific application.

An adapted reconstruction algorithm combines the sequential 'frozen motion volumes' (from the different sub-arrays) by separate reconstruction and modelling of moving and static parts in the patient and visualizes them as moving 2D or 3D images/volumes depending on the need of the physician.

Shown in the upper half of FIG. 7 is an example of a detector surface divided into several sub-areas. The six portions or sub-areas of the detector, divided by the thick lines, may be different parts of a detector. Furthermore, those parts may be inclined relative to each other, as for example illustrated in FIG. 8, in one or in two directions. As indicated in grey scale in FIG. 7, i.e. as darkened sections of the detector surface, sub-areas may be defined which extend over more than one part of the detector when radiation is emitted onto these sub-areas. Furthermore, an anti-scattering grid may be provided on the detector, as indicated by the parallel thin lines on the detector surface. Preferably, the grid lines are focused towards the corresponding line of sources that illuminate the corresponding detector area.

Figures 8, 9:
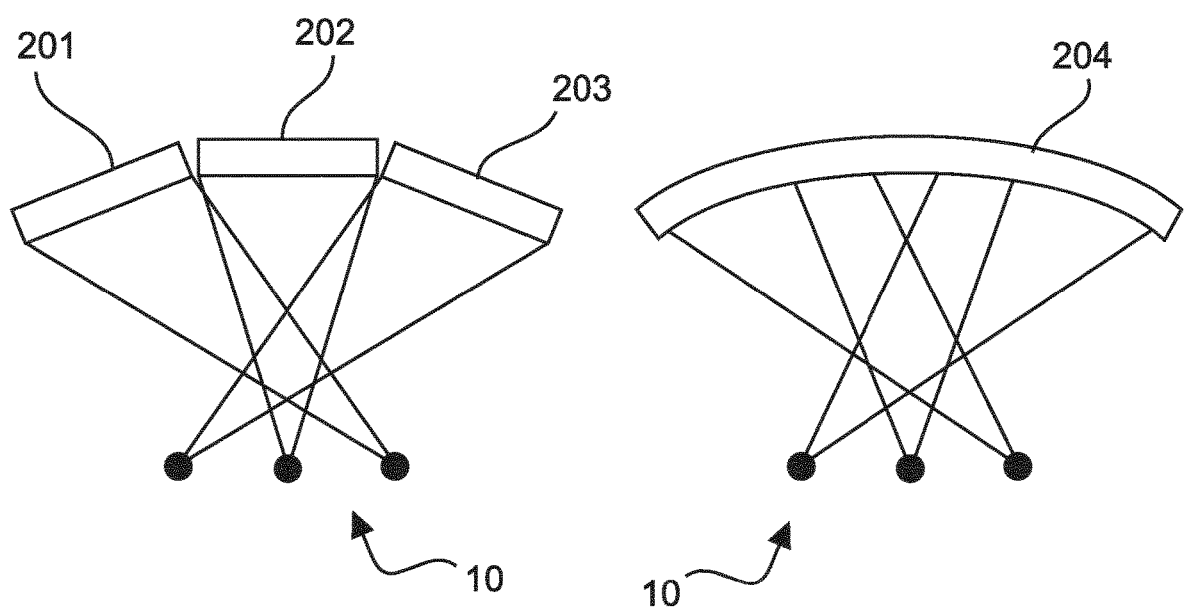
FIG. 8 illustrates aspects of a third embodiment of a system.
FIG. 9 illustrates aspects of a fourth embodiment of a system.

FIG. 8 shows an embodiment with a segmented detector. The detector is formed by detector parts 201, 202 and 203 which parts are arranged in direct vicinity to each other, i.e. even with abutting edges. Each of the detector parts is formed as a flat detector. In this embodiment, the detector parts are arranged so that one radiation source is associated with one of the detector parts, wherein the radiation emitted by the radiation sources 10 intersect each other in a region of interest in a patient's body. Corresponding to the aspect that the outer radiation sources emit the radiation with an angle to a main radiation direction, the outer parts of the detector are inclined to better receive the radiation. For example, grid lines of the grid part belonging to detector part 203 may preferably be focused towards the line of sources indicated by the left source in FIG. 8.

FIG. 9 shows another embodiment with a curved detector. Also here, the radiation from the outer radiation sources may be better received by the detector with the outer portions of the detector 204 having a surface normal which is inclined relative to the main radiation direction of the radiation array 10.

As a further aspect, the controlling as well as the reconstruction of images based on the detected radiation may be implemented as a computer program executable on a processor of the system. Such a computer program may be provided on a suitable medium such as an optical storage medium or a solid-state medium supplied together with or as part of the processor, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS

10 multiblock
20, 204 detector
201, 202, 203 detector parts
30 patient table
11, 12, 13 radiation sources
21, 22, 23 radiation sources
31, 32, 33 radiation sources
41 radiation source
X1, X2, X3 radiation sources
1Y, 2Y, 3Y radiation sources
XY radiation source

The invention claimed is:

1. A system, comprising:
   a plurality of X-ray radiation sources; and
   an X-ray radiation detector,
   wherein a first group of first X-ray radiation sources out of the plurality of X-ray radiation sources simultaneously emit X-ray radiation onto a first pattern of first sub-areas of the X-ray radiation detector, wherein the first sub-areas of the first pattern do not overlap each other, and wherein each of the first X-ray radiation sources emits X-ray radiation onto a corresponding one of the first sub-areas of the X-ray radiation detector,
   wherein a second group of second X-ray radiation sources out of the plurality of X-ray radiation sources simultaneously emit X-ray radiation onto a second pattern of second sub-areas of the X-ray radiation detector, wherein the second sub-areas of the second pattern do not overlap each other, and wherein each of the second X-ray radiation sources emits X-ray radiation onto a corresponding one of the second sub-areas of the X-ray radiation detector, and
   wherein at least some of the first sub-areas of the first pattern only partially overlap at least some of the second sub-areas of the second pattern,
   wherein the plurality of X-ray radiation sources defines a main radiation direction, and wherein at least one X-ray radiation source among the first group of first X-ray radiation sources or the second group of second X-ray radiation sources is arranged so that a first radiation direction of the one X-ray radiation source is inclined relative to the main radiation direction with an angle of greater than 0° and less than 50°.

2. The system of claim 1, further comprising a control unit configured to control a switching sequence of X-ray radiation emission from the first and second groups of X-ray radiation sources and further configured to carry out sequential switching between the first group of first X-ray radiation sources and the second group of second X-ray radiation sources.

3. The system of claim 2, wherein the plurality of X-ray radiation sources are arranged in a matrix, and wherein the second X-ray radiation sources of the second group of X-ray radiation sources are arranged along a first direction of the matrix and are arranged with a distance from the first X-ray radiation sources of the first group of X-ray radiation sources in a second direction which is orthogonal to the first direction.

4. The system of claim 1, wherein the plurality of X-ray radiation sources includes a further group of X-ray radiation sources, wherein the further group of X-ray radiation sources simultaneously emit X-ray radiation onto a further pattern of sub-areas of the detector, and wherein at least some of the sub-areas of the further pattern overlap at least some of the first sub-areas of the first pattern and/or at least some of the second sub-areas of the second pattern.

5. The system of claim 1, further comprising a plurality of high voltage generator units providing different voltages for different ones of the plurality of X-ray radiation sources and/or means for providing fast kV switching.

6. The system of claim 1, further comprising an anti-scattering grid at the X-ray radiation detector.

7. The system of claim 1, wherein the first radiation direction is inclined relative to the main radiation direction with an angle of 45°, and wherein at least an other X-ray radiation source among the first group of first X-ray radiation sources or the second group of second X-ray radiation sources is arranged so that a second radiation direction of the other X-ray radiation source is inclined relative to the main radiation direction with an angle of 45°, and wherein the first radiation direction and second radiation direction are perpendicular to each other, and wherein the one X-ray radiation source and the other X-ray radiation source are configured to be controlled to emit X-ray radiation at a same time as each other.

8. The system of claim 7, wherein the plurality of X-ray radiation sources includes a further group of X-ray radiation sources, wherein the further group of X-ray radiation sources simultaneously emit X-ray radiation onto a further pattern of sub-areas of the detector, and wherein at least some of the sub-areas of the further pattern overlap at least some of the first sub-areas of the first pattern and/or at least some of the second sub-areas of the second pattern, and wherein at least a further one of the further group of X-ray radiation sources is arranged so that a third radiation direction of the further one X-ray radiation source is in the main radiation direction, and wherein the one X-ray radiation source, and the other X-ray radiation source, and the further one X-ray radiation source are configured to be controlled to emit X-ray radiation at a same time as each other.

9. A method, comprising:
emitting simultaneously X-ray radiation from a first group of first X-ray radiation sources among a plurality of X-ray radiation sources;
detecting the emitted radiation from the first group of first X-ray radiation sources on a first pattern of sub-areas of an X-ray radiation detector, wherein the first sub-areas of the first pattern do not overlap each other, and wherein each of the first X-ray radiation sources emits X-ray radiation onto a corresponding one of the first sub-areas of the X-ray radiation detector;
emitting simultaneously X-ray radiation from a second group of second X-ray radiation sources among the plurality of X-ray radiation sources; and
detecting the emitted X-ray radiation from the second group of second X-ray radiation sources on a second pattern of second sub-areas of the X-ray radiation detector, wherein the second sub-areas of the second pattern do not overlap each other, and wherein each of the second X-ray radiation sources emits X-ray radiation onto a corresponding one of the second sub-areas of the X-ray radiation detector,
wherein at least some of the first sub-areas of the first pattern only partially overlap at least some of the second sub-areas of the second pattern,
wherein the plurality of X-ray radiation sources defines a main radiation direction, further comprising at least one X-ray radiation source among the first group of first X-ray radiation sources or the second group of second X-ray radiation sources emitting X-ray radiation in a first radiation direction which is inclined relative to the main radiation direction with an angle of greater than 0° and less than 50°.

10. The method of claim 9, further comprising:
reconstructing a first image based on the X-ray radiation detected in all of the first sub-areas of the first pattern; and
reconstructing a second image based on the X-ray radiation detected in all of the second sub-areas of the second pattern.

11. The method of claim 9, further comprising providing different high voltages to different X-ray radiation sources for spectral decomposition.

12. The method of claim 9, wherein emitting X-ray radiation from the first group and from the second group are performed in a switching sequence, wherein switching between the first group and the second group occurs within 30 ms.

13. The method of claim 9, further comprising reconstructing 3D image information based on the detected X-ray radiation of at least two of the plurality of X-ray radiation sources, wherein a first radiation direction of a first of the two X-ray radiation sources is inclined relative to a second radiation direction of a second of the two radiation sources.

14. The method of claim 9, wherein the first radiation direction is inclined relative to the main radiation direction with an angle of 45°, and further comprising at least an other X-ray radiation source among the first group of first X-ray radiation sources or the second group of second X-ray radiation sources emitting X-ray radiation in a second radiation which is inclined relative to the main radiation direction with an angle of 45°, and wherein the first radiation direction and second radiation direction are perpendicular to each other, and wherein the one X-ray radiation source, and the other X-ray radiation source emit X-ray radiation at a same time as each other.

15. A system, comprising:
a plurality of X-ray radiation sources;
an X-ray radiation detector; and
a control unit,
wherein a first group of first X-ray radiation sources out of the plurality of X-ray radiation sources simultaneously emit X-ray radiation onto a first pattern of first sub-areas of the X-ray radiation detector, wherein the first sub-areas of the first pattern do not overlap each other, and wherein each of the first X-ray radiation sources emits X-ray radiation onto a corresponding one of the first sub-areas of the X-ray radiation detector,
wherein a second group of second X-ray radiation sources out of the plurality of X-ray radiation sources simultaneously emit X-ray radiation onto a second pattern of second sub-areas of the X-ray radiation detector, wherein the second sub-areas of the second pattern do not overlap each other, and wherein each of the second X-ray radiation sources emits X-ray radiation onto a corresponding one of the second sub-areas of the X-ray radiation detector, wherein at least some of the first sub-areas of the first pattern only partially overlap at least some of the second sub-areas of the second pattern, and wherein the control unit is configured to control the plurality of X-ray radiation sources to activate the first group of first X-ray radiation sources and deactivate the second group of second X-ray radiation sources within a first exposure time period, and to activate the second group of second X-ray radiation sources and deactivate the first group of first X-ray radiation sources within a second exposure time period which is subsequent to the first time period, wherein at least one X-ray radiation source of the first group of first X-ray radiation sources or of the second group of second X-ray radiation sources is arranged so that a first radiation direction of the one X-ray radiation source is inclined by 45 degrees relative to a second radiation direction of an other one of the first group of first X-ray radiation sources or of the second group of second X-ray radiation sources.

16. The system of claim 15, further comprising a plurality of high voltage generator units providing different voltages for different ones of the plurality of X-ray radiation sources.

17. The system of claim 15, further comprising an anti-scattering grid at the X-ray radiation detector.

18. The system of claim 15, wherein the control unit is configured to switch between the first exposure time period and the second exposure time within 16 ms.

19. The system of claim 15, wherein the plurality of X-ray radiation sources are arranged in a matrix, and wherein the second X-ray radiation sources of the second group of X-ray radiation sources are arranged along a first direction of the matrix and are arranged with a distance from the first X-ray radiation sources of the first group of X-ray radiation sources in a second direction which is orthogonal to the first direction.

20. The system of claim 15, wherein the plurality of X-ray radiation sources includes a further group of X-ray radiation sources, wherein the further group of X-ray radiation sources simultaneously emit X-ray radiation onto a further pattern of sub-areas of the detector, wherein at least a further one of the further group of X-ray radiation sources is arranged to emit X-ray radiation in a third radiation direction, wherein the third radiation direction is inclined relative to the first radiation direction by 45 degrees, wherein the third radiation direction is inclined relative to the second radiation direction by 90°, and wherein the control unit is configured to control the one X-ray radiation source, and the other X-ray radiation source, and the further one X-ray radiation source to emit X-ray radiation at a same time as each other.

* * * * *